US00PP36595P3

(12) United States Plant Patent
Bouchet

(10) Patent No.: US PP36,595 P3
(45) Date of Patent: Apr. 15, 2025

(54) YELLOW NECTARINE TREE NAMED 'NECTAMILA'

(50) Latin Name: ***Prunus persica* var *nucipersica* (L.) Batsch.**
Varietal Denomination: NECTAMILA

(71) Applicant: AGRO SELECTIONS FRUITS, Elne (FR)

(72) Inventor: Christophe Bouchet, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 18/445,621

(22) Filed: Nov. 28, 2023

(65) Prior Publication Data

US 2024/0180051 P1 May 30, 2024

(30) Foreign Application Priority Data

Nov. 29, 2022 (QZ) ..... PBR 2022/2716

(51) Int. Cl.
*A01H 5/08* (2018.01)
*A01H 6/74* (2018.01)

(52) U.S. Cl.
USPC ..... Plt./190
CPC ..... *A01H 6/7454* (2018.05); *A01H 5/08* (2013.01)

(58) Field of Classification Search
USPC ..... Plt./190
CPC ..... A01H 5/08; A01H 5/00; A01H 6/7454; A01H 6/74
See application file for complete search history.

(56) References Cited

U.S. PATENT DOCUMENTS

PP17,480 P3 * 3/2007 Maillard ..... A01H 6/7454 Plt./190

* cited by examiner

*Primary Examiner* — June Hwu
(74) *Attorney, Agent, or Firm* — Birch, Stewart, Kolasch & Birch, LLP

(57) ABSTRACT

A new and distinct variety of yellow nectarine tree denominated 'NECTAMILA' which has fruits with high eating quality, meaning a taste perception of high sugar content and developed aromas, and very long shelf life without alteration before and after harvesting, with a semi-sweet orange yellow flesh at maturity time, with varying degrees of red pigmentation depending on maturity, and an attractive skin with a very high percentage of luminous purple red blush on skins surface, on a red or orange red background.

4 Drawing Sheets

Botanical classification: *Prunus persica* var *nucipersica* (L.) Batsch.

Variety denomination: 'NECTAMILA'.

This application claims priority of Community Plant Variety Right No. 2022/2716 filed on Nov. 29, 2022 (11/29/2022) which is hereby incorporated by reference in its entirety.

The new variety named 'NECTAMILA' is also known as 24.01.59.15 NJ or ASF2024. Indeed, before giving a name to a new and distinct variety of fruit tree, a provisional reference is assigned, considering the references of a tree in orchard. This provisional reference is constituted firstly with the number of the parcel on which the tree has grown, then the number of the line, the tree number and finally the year of selection. Then before being named 'NECTAMILA', the provisional reference of this yellow nectarine tree variety was 24.01.59.15, corresponding to the tree 59 located in line 01 of the parcel 24 and selected during the year 2015. The letters "NJ" are related to the first letters of the type of tree in French (NJ for "Nectarine Jaune", that means "yellow nectarine"). Once the hybrid selected, the breeder assigned a clone reference that begins with the letters "ASF" followed by the year of selection and a number corresponding to the maturity order. The final name is only assigned once the application has been filed and the name approved after its publication in the official bulletin. For the variety 'NECTAMILA', the clone reference was 'ASF2024'.

BACKGROUND OF THE NEW VARIETY

The present invention relates to a new and distinct variety of yellow nectarine tree, *Prunus persica* (L.) Batsch, which has been given the variety denomination 'NECTAMILA'.

This new tree produces fruits with a long shelf life without alteration both on the tree after growth completion and after harvesting, very good eating quality, which means a taste perception of high sugar content and developed aromas, semi-clingstone yellow orange flesh fruits, with varying degrees of red pigmentation depending on the ripeness of the fruit, for fresh market at the end of July or early in August in the Pyrénées-Orientales department, France.

ORIGIN OF THE VARIETY

The 'NECTAMILA' yellow nectarine tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen. Summer is dry with a few thunderstorms.

The 'NECTAMILA' variety results from a controlled pollinated cross between the white nectarine variety named 'NECTARTIC' (U.S. Plant Pat. No. 23,442) which was used as the seed parent, or female parent, and the white flat nectarine variety named 'CAKELOVE' (U.S. Plant Pat. No. 24,107) which was used as the pollen parent, or male parent.

The 'NECTAMILA' variety was obtained by hybridizing and propagated by grafting on a 'INRA® GF677' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree, and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'NECTAMILA' yellow nectarine tree blooms at the end of February near Elne in the Pyrénées-Orientales department, France. The blooming period is considered medium. However, it was observed that its date of blooming seems to be highly dependant on climatic conditions.

The first fruit of 'NECTAMILA' ripens generally medium in the season, namely in the during the last two weeks of July. However, it was observed that its date of maturity seems to be highly dependant on climatic conditions.

DESCRIPTION OF THE DRAWINGS

In the accompanying drawing, which are as nearly true as it is reasonably possible to make in a color illustration of this type.

Figure 1:
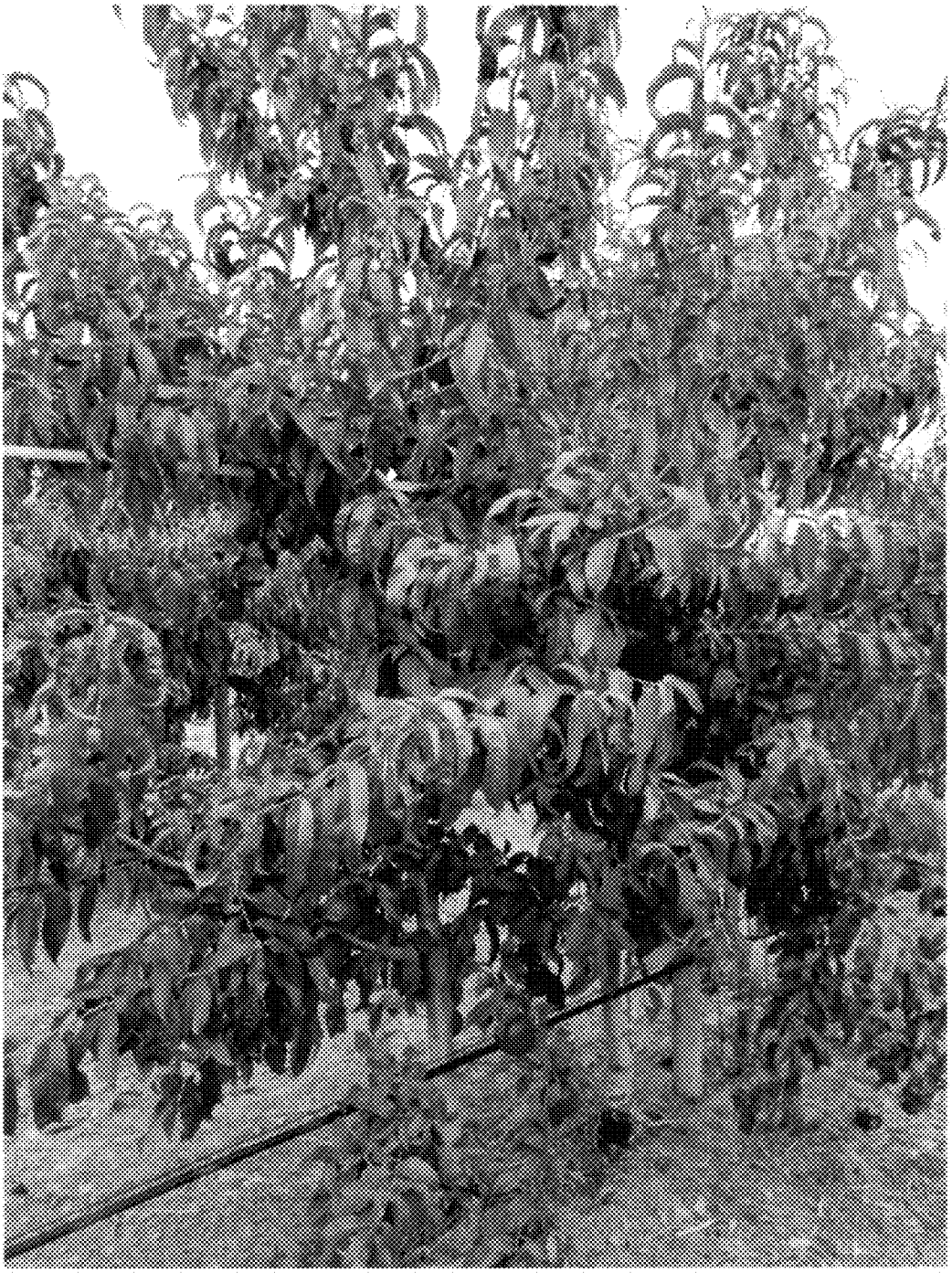
FIG. 1 is a color photograph showing trees of the new variety 'NECTAMILA' in orchard, bearing fruits.
Figure 2:
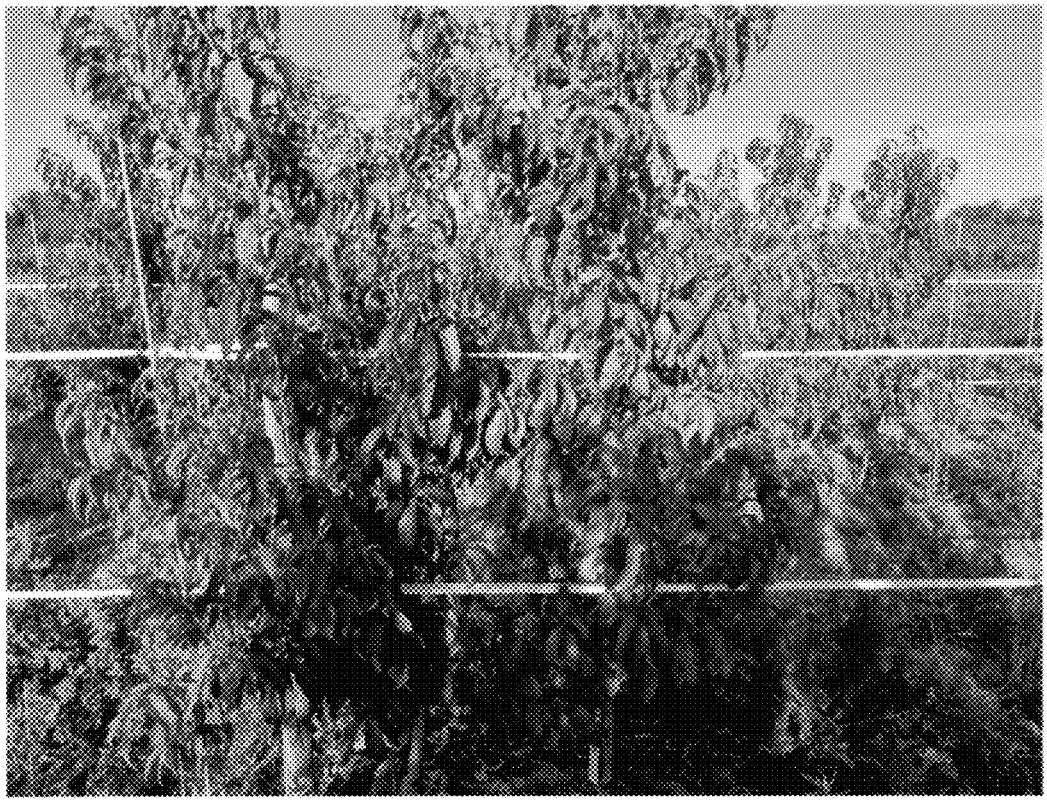
FIG. 2 is another color photograph showing trees of the new variety 'NECTAMILA' in orchard, bearing fruits.
Figure 3:
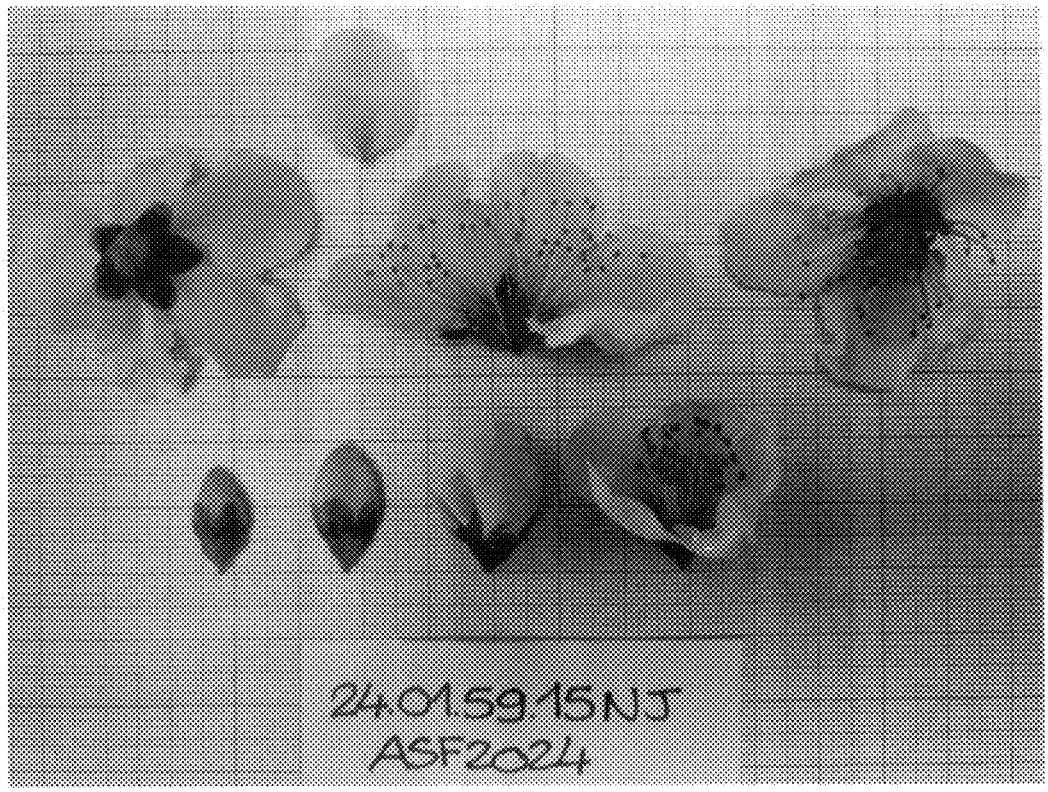
FIG. 3 is a color photograph which depicts the flower buds at different development stages, and the reverse and side views of the flower and the reproductive organs with petals removed, of the new variety 'NECTAMILA' also named '24.01.59.15 NJ' or 'ASF2024' as indicated in FIG. 3.
Figure 4:
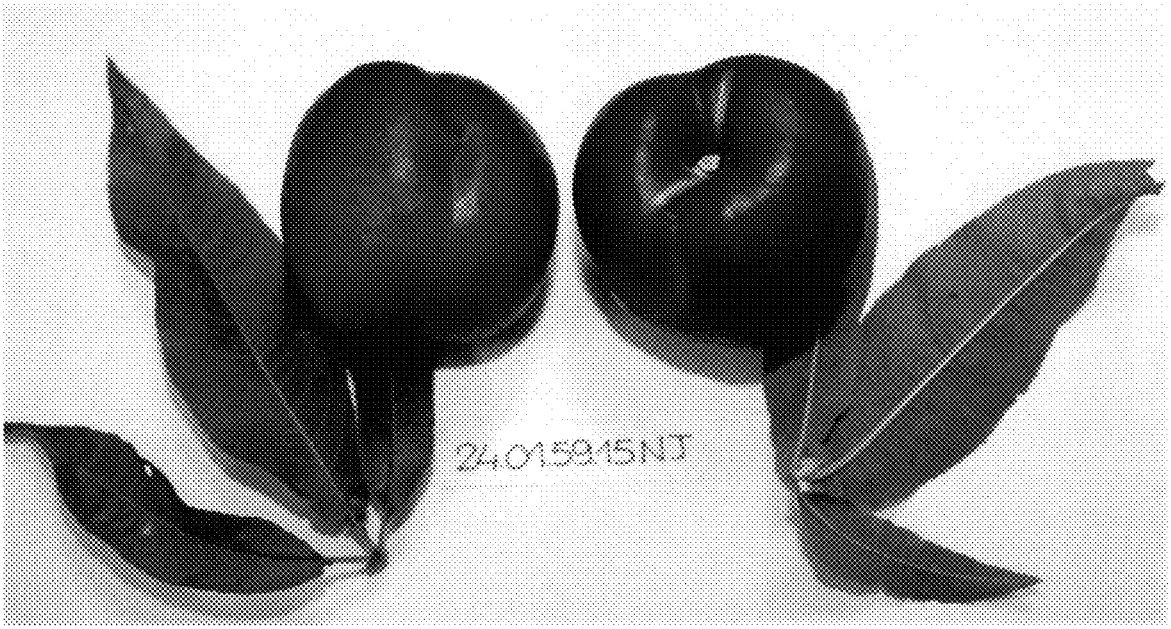
FIG. 4 is a color photograph which shows the upper and lower sides of leaves and different views of two typical specimens of the fruit of the new variety 'NECTAMILA' also named '24.01.59.15 NJ' at ripening time, for depicting leaves and fruit skin of the new variety.
Figure 5:
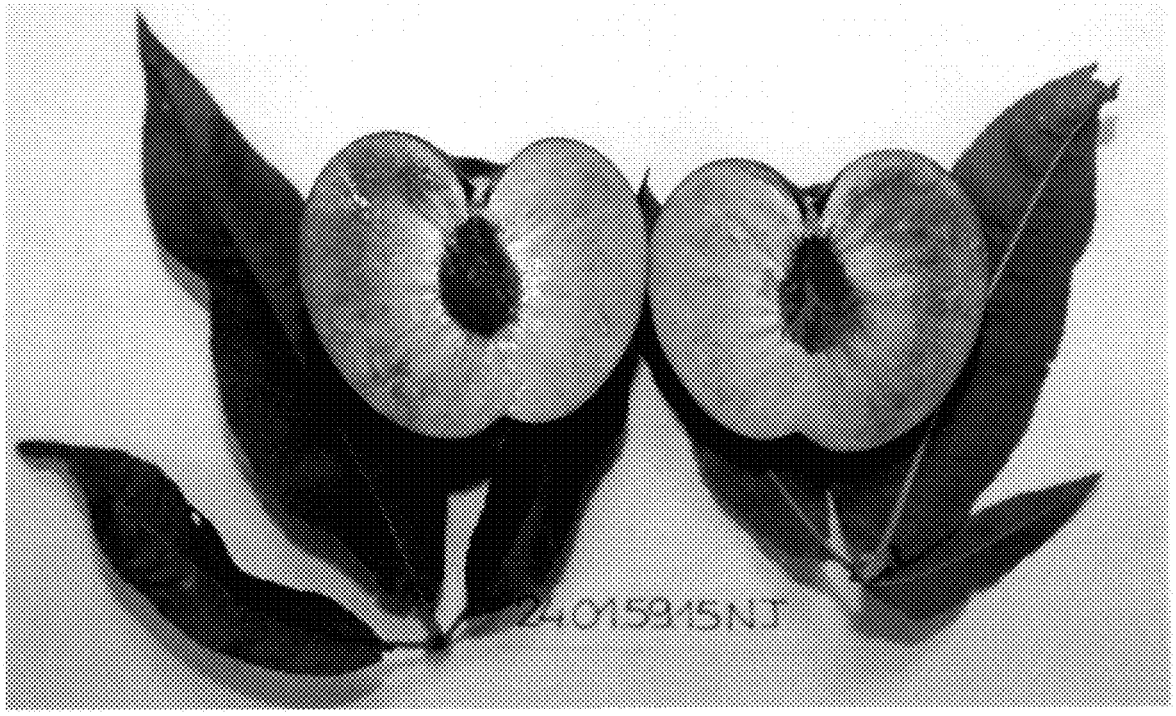
FIG. 5 is a color photograph which shows the upper and lower sides of leaves and one fruit of the new variety 'NECTAMILA' also named '24.01.59.15 NJ' at ripening time, the fruit having been cut in half with the pit being left in one of the halves for depicting leaves, fruit flesh, pit and pit cavity of the new variety.
Figure 6:
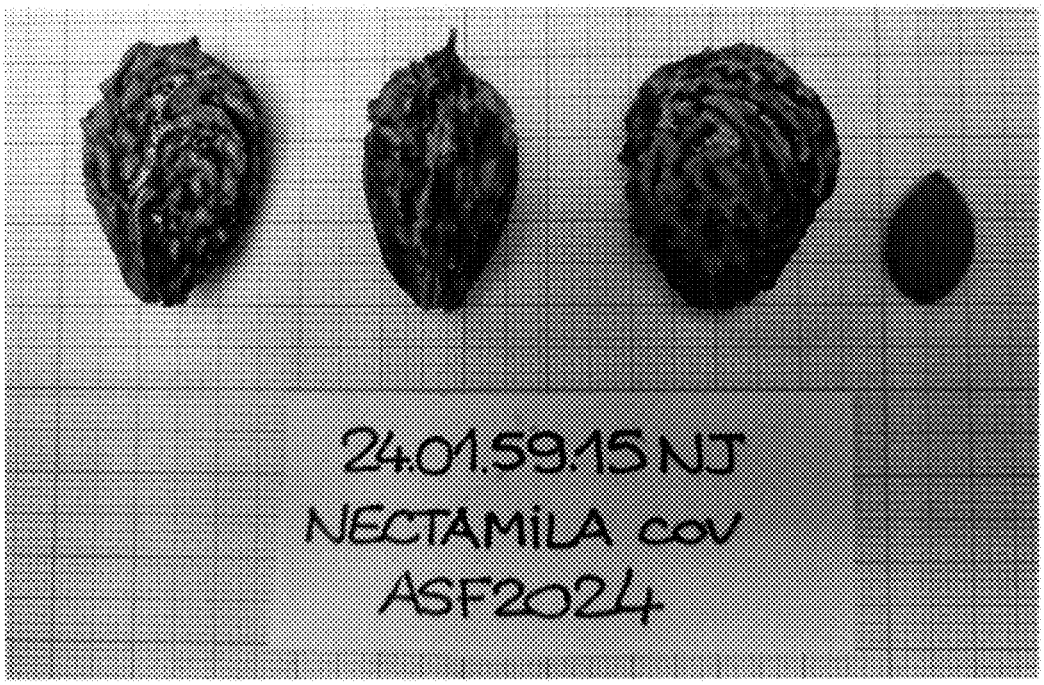
FIG. 6 is a color photograph showing different views of the stone of the new variety 'NECTAMILA' also named '24.01.59.15 NJ' or 'NECTAMILA cov' or 'ASF2024' as shown in the photograph, and the kernel of the stone.

The views of trees, flowers, leaves and fruits have been photographed in their fourth growing season (third year of production).

Due to chemical development, processing and printing, the flowers, stones and fruits depicted in these photographs may or may not be accurate when compared to the actual botanical specimen.

DETAILED BOTANICAL DESCRIPTION

The trees, flowers, and fruits may vary in slight detail due to variations in soil type, cultural practices, and climatic condition. The potential for commercial production of fresh fruits by 'NECTAMILA' is high, due to fruit very long shelf life without alteration after harvesting.

Trees are medium to strong vigorous and large stature half-standing in a semi-flared out aspect. The anthocyanic coloration of flowering shoot is present excluding brushwood side away from sun. The time of beginning of flowering is considered medium; flowering typically starts at the end of February. The type of flower is showy (rosette) with medium petal size. Petals are pink. Leaf glands are present and reniform. The fruit flesh is yellow orange at complete maturity, with more or less red pigmentation depending on the ripeness of the fruit. The fruit skin is medium thick, with a luminous purple red blush on a red to orange red background. The stone is semi-clingstone and its size is medium. Fruit taste is semi-sweet, aromatic and with a high level of sugars.

Compared to 'NECTAVANTOP' yellow nectarine variety (U.S. Plant Pat. No. 22,493), the fruits of 'NECTAMILA' usually ripen approximately one week earlier than the fruits of 'NECTAVANTOP'. Moreover, the fruit size of 'NECTAMILA' is slightly higher than the fruit size of the similar variety 'NECTAVANTOP'. It should be noted that observations of fruit size can vary from one year to the next, depending, others, on growing conditions, specific features of the year especially regarding weather conditions, among other factors. It is however remarkable that, on average and considering equal conditions, the fruits of the new variety 'NECTAMILA' are higher in size than the fruits of 'NECTAVANTOP'.

Compared to 'NECTAREINE' yellow nectarine variety (U.S. Plant Pat. No. 17,480), the fruits of 'NECTAMILA' ripens approximately at the same period. The flowering period of the new variety 'NECTAMILA' is however about ten days earlier than the flowering period of the similar variety 'NECTAREINE'.

In addition, the fruit skin of the new variety 'NECTAMILA' has a darker and more purple-red color than the fruit skin of the similar variety 'NECTAREINE', the latter being light red. Particularly, the fruit skin of 'NECTAMILA' is much more colorful and has fewer lenticels than the fruit skin of 'NECTAREINE'. The coloration of the fruit skin for the new variety is brighter and more uniformly colored. The fruit shape is rounder and more homogeneous for 'NECTAMILA'. As a result of all the above, the fruit of the new variety has a better appearance than fruit of the 'NECTAREINE' variety.

Compared to its seed or female parent, i.e., the 'NECTARTIC' (U.S. Plant Pat. No. 23,442) variety, the new variety 'NECTAMILA' ripens usually approximately one month earlier. The flowering period of the new variety 'NECTAMILA' is similar to the flowering period of the parent variety 'NECTARTIC'. It should also be noted that the new 'NECTAMILA' variety corresponds to a yellow nectarine variety, whereas the fruits of the parent variety 'NECTARTIC' have a white flesh.

Compared to its pollen or male parent, i.e., the 'CAKELOVE' (U.S. Plant Pat. No. 24,107) variety, the new variety 'NECTAMILA' ripens usually approximately ten days later. The flowering period of the new variety 'NECTAMILA' is also later than the flowering period of the parent variety 'CAKELOVE', by around two to three weeks. It should also be noted that the new 'NECTAMILA' variety corresponds to a yellow nectarine variety, whereas the 'CAKELOVE' variety corresponds to a white flat nectarine.

The new 'NECTAMILA' variety is thus distinguished from its progenitors by its subspecies, flowering date and ripening date.

DETAILED DESCRIPTION

Referring more specifically to the pomological details of this new and distinct variety of yellow nectarine tree, the following was observed on trees in their fourth growing season (third year of production), except for the observations on flower which were done in the third growing season, under the ecological conditions prevailing at the orchards located near the town of Elne, Pyrénées-Orientales departement, France. All observations have been done on rootstock cultivars. Used rootstocks were 'INRA® GF677' (non-patented) trees. All major color code designations are by reference to The R.H.S. Colour Chart (Fourth Edition) provided by The Royal Horticultural Society of Great Britain.

Tree:

*Size*.—Generally — Considered large. The tree size the first year was approximately 200 to 280 cm in height. The tree was pruned during each following dormant season to a height of approximately 250 cm. Current season shoots growth could reach 80 cm in length. The tree size from the second year (second and next years) reached a final height of 330 cm including current season shoots length. The tree size is consistently reduced to 250 cm the next years.

*Spread*.—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor*.—Considered medium to strong.

*Productivity*.—Considered good to very good, and regular. Fruit set is spaced by thinning to develop the remaining fruit into the desired market sized fruit. The number of the fruit set varies with the prevailing climatic conditions and cultural practices employed during the bloom period and is therefore not distinctive of the present variety. A reduce vegetation, obtained with pruning or green pruning, approximately 1 month or 1 month ½ before harvesting fruits, significantly promotes fruit qualities, especially growth, color and firmness. Moreover, contamination risks due to monilia or rot are significantly reduced. 'NECTAMILA' variety is not much sensitive to cracking of pistil cavity, to cork formation into peduncle cavity or to monilia.

*Bearer*.—Very regular. The fruit distribution is considered homogenous on mixed branches and spurs having more than 1 year. Thinning of 2 fruits out of 3 was necessary for the tree valorisation. Thinning was necessary every year during the years of observation.

*Form*.—The 'NECTAMILA' variety has naturally a semi-flared shape.

*Density*.—Considered dense.

*Tree branching*.—Medium to strong.

*Hardiness*.—Hardy in all stone fruit growing areas of France and especially where the chilling requirement is between 700 and 1200 hours. More particularly, experimentations on the same orchard in Elne, Pyrénées-Orientales department, with winter chilling requirement below 7.2° C. comprised between 700 hours and 1200 hours according to the specificities of the year, namely 1031 hours in 2012-2013, 777 hours in 2013-2014, 893 hours in 2014-2015, 718 hours in 2015-2016, 825 hours in 2016-2017, 1017 hours in 2017-2018, 844 hours in 2018-2019, 706 hours in 2019-2020, 822 hours in 2020-2021, 700 hours in 2021-2022 and 919 hours in 2022-2023 showed a good behavior of the tree in all cases. No injury with temperatures as low as −12° C. in winter. Good resistance to late frosts.

Trunk:

*Diameter*.—Approximately 48.0 to 52.0 millimeters in diameter when measured at a distance of approximately 20.0 centimeters above the soil level for trees on fourth leaf (or third year of production).

*Bark texture*.—Considered rough, with lenticels.

*Lenticels*.—Lenticels are present. The number of lenticels reaches 1 lenticel per $cm^2$. The lenticels range in size of approximately 4.0 to 5.0 millimeters in width, and about 1.0 to 1.5 millimeter in height.

*Lenticel color*.—The lenticels show a beige color (RHS Greyed Orange 165 B or RHS Greyed Orange 165 C).

*Bark coloration*.—The bark has a brown to grey color (RHS Greyed Orange 177 A or RHS Grey 201 B) darker than the lenticels color.

Branches:

*Size*.—The branches are pruned to approximately 1.0 meter in length.

*Diameter*.—Average as compared to other nectarine varieties. The current season shoots have a diameter of approximately 3.0 to 6.0 millimeters, and mature branches have a diameter of approximately 5.0 to 8.0 millimeters.

*Surface texture*.—Smooth, despite the presence of small lenticels, for current season shoots and rough, with lenticels, for mature branches, wood which is several years old has furrowed appearance.

*Crotch angles*.—Primary branches are considered variable, but the crotch angles are generally 45 degrees from the horizontal axis for current season shoots and 75° degrees from the horizontal axis for two year's old branches. This particular characteristic is not considered distinctive of the variety, however.

*Current season shoots.*—

*Internode length.*—Generally 20.0 to 22.0 millimeters. Color. — The color of new shoot tips is considered green (RHS Yellow Green 144 B) on lower part of new shoot tips, whereas the upper part is darker and colored in purple (RHS Greyed Purple 184 A or RHS Greyed Purple 184 B).

*Mature branches.*—

*Internode length.*—Generally 24.0 to 28.0 millimeters.

*Color of mature branches.*—Brown (RHS Grey Brown 199 A).

*Lenticels.*—Lenticels are present on mature branches. The number of lenticels reaches 0,5 lenticel per $cm^2$. The size of lenticels is considered small on one year's old shoots and small on two-year-old shoots. The lenticel shape is round with a diameter of approximately 1.0 millimeter on one-year-old shoots and stretched round with a diameter of 1.5 millimeters on two-year-old shoots. The lenticel may have a height of 1.0 millimeter and a width of 2.0 millimeters.

*Lenticel color.*—The lenticels on branches have a beige color (RHS Greyed Orange 165 B or RHS Greyed Orange 165 C).

Leaves:

*Time of beginning of leaf bud burst.*—Considered medium.

*Size.*—Considered medium for the species. The ratio leaf length/leaf width is 3.52.

*Leaf length.*—The medium length is about 169.8 millimeters with leaf petiole.

*Leaf width.*—The medium width is 48.25 millimeters.

*Leaf form (in cross section).*—Concave.

*Leaf form.*—Entire.

*Leaf base shape.*—Attenuated, i.e., the blade is tapered towards its base.

*Leaf tip form.*—Aristulate.

*Leaf thickness.*—Medium.

*Leaf color.*—Upper leaf surface. — Yellow Green (RHS Yellow Green 147 A). Lower surface. — A slightly lighter green (RHS Yellow Green 146 A or RHS Yellow Green 146 B) than the upper leaf surface color.

*Leaf texture.*—Smooth and glabrous on both upper and lower surfaces of the leaf.

*Leaf venation.*—Pinnately veined.

*Mid-vein.*—Color. — Light green (RHS Yellow Green 153 A) on both upper and lower leaf surfaces. Width. — Approximately 1.5 millimeters.

*Secondary veins.*—Color. — Light green (RHS Yellow Green 145 C) on both upper and lower leaf surfaces.

*Leaf margins.*—Slightly undulating.

*Form.*—Considered crenate.

*Uniformity.*—Leaves are isolated or grouped by 2 or 3. In this last case, one leaf of normal size is found with one or two smaller leaves (at least 50% smaller).

*Leaf petioles.*—Size. — Considered medium. Length. — About 11.0 to about 12.0 millimeters. Diameter. — About 2.0 to 2.5 millimeters. Shape. — Grooved.

*Petiole color.*—Upper petiole surface. — Green (RHS Yellow Green 145 A). Lower surface. — A slightly lighter green (RHS Yellow Green 151 D) than the upper petiole surface color. Ratio between leaf blade length and petiole length. — About 14.

*Leaf glands.*—Size. — Considered medium. Their length is about 2.0 millimeters and their width is about 1.0 millimeter. Number. — Generally 2 or 3 glands per leaf. Type. — Reniform. Margins. — Smooth. Position. — Alternate on the upper part of petiole. Color. — On young leaves, leaf glands color is considered a light green (RHS Yellow Green 145 A). On older leaves, leaf glands color turns to a brown (RHS Greyed Orange 165 A) color.

*Leaf stipules.*—Generally. — No leaf stipules were observed. But as seen in the characteristic relative to the leaves uniformity, it is possible to find leaves by groups of 2 or 3, with a normal-size leaf and smaller ones.

Flowers:

*Flower buds.*—Generally. — At pre-floral stage of development, the floral buds are round in shape. Their form is evolving until blooming, with variable dimensions. Just before blooming, floral buds are approximately 11.0 to 13.0 millimeters wide and approximately 13.0 to 15.0 millimeters long. The floral buds show a homogenous distribution on the trees. Color. — This characteristic is dependent upon the proximity to bloom. At pre-floral stage of development, the bottom of the flower's buds, or calyx, or flower receptacle, is of purple color (RHS Greyed Purple 187 A) on its outer face. The inner face of the flower receptacle is orange (RHS Orange 26 A). The corolla, formed by the petals, is generally of pink color (RHS Red Purple 65 B) on both faces. Petals color shows an evolution until the end of flowering.

*Hardiness.*—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—The blooming time generally begins in February. The first bloom was observed on Feb. 26, 2021.

*Blooming time.*—Considered medium in relative comparison to other commercial nectarine cultivars grown in the Pyrénées-Orientales departement, France. The date of full bloom is observed generally at the middle of the blooming period. The date of bloom varies slightly with climatic conditions and cultural practices. Thus, the full bloom was observed from February $26^{th}$ to Mar. 3, 2021, from February $20^{th}$ to Feb. 27, 2022, from March $6^{th}$ to Mar. 14, 2023.

*Duration of bloom.*—Medium, approximately 8 days. This characteristic varies slightly with the prevailing climatic conditions.

*Flower type.*—The variety is considered to have a showy (or rosette) type of flower.

*Flower size.*—Considered medium. Flower diameter at full bloom is approximately 29.0 to 35.0 millimeters.

*Bloom quantity*.—Considered high, approximately 35 to 40 flowers per meter, with a high rate of fruit set.

*Flower bud frequency*.—Generally 2 flower buds appear per node, occasionally 1.

*Petal size*.—Generally. — Considered medium.

*Length*.—Generally between 19.0 and 22.0 millimeters.

*Width*.—Generally between 19.0 and 20.0 millimeters.

*Petal form*.—Round-shaped.

*Petal count*.—Usually five.

*Petal arrangement*.—Intermediate tangents, which means that some petals overlap.

*Petal texture*.—Smooth on both upper and lower surfaces of the petal.

*Petal color*.—At the stage F of blooming, when the flower is fully opened, both surfaces of the petal are colored with a pink (RHS Red Purple 65 B) color.

*Fragrance*.—Moderate, floral fragrance.

*Petal claw*.—Form. — The claw is considered to have a narrow form. Length. — About 1.0 millimeter. Width. — About 1.0 millimeter at the base. Color. — The petal claw usually shows a pink color darker than the petal color (RHS Red Purple 60 A).

*Petal margins*.—Generally considered slightly undulating.

*Petal apex*.—Generally. — The petal apices are generally round shaped.

*Flower pedicel*.—Length. — Considered medium and having an average length of approximately 2.0 to 3.0 millimeters. Diameter. — Considered average, approximately 1.0 millimeter. Color. — Green (RHS Yellow Green 144 A or RHS Yellow Green 144 B).

*Calyx*.—Internal surface texture. — Smooth. Color. — At the stage F of blooming, when the flower is opened, the inner surface of the calyx, namely the flower receptacle, is orange (RHS Orange N25 C). The outer surface of the calyx is considered of purple color (RHS Greyed Purple 187 A or RHS Greyed Purple 187 B).

*Sepals*.—

*Sepal count*.—Usually 5 sepals. Surface texture. — The outer surface has a short, fine pubescent texture. Margins. — Smooth. Size. — Medium. Length. — Approximately 5.0 to 6.5 millimeters. Width. — Approximately 4.0 to 5.5 millimeters. Form. — Conic and round at the top. Color. — The upper surface of the sepals shows a purple color (RHS Greyed Purple 187 A) whereas the lower surface of sepals is considered greenish (RHS Yellow Green 146 A or RHS Yellow Green 146 B).

*Anthers*.—Generally. — Medium in length, approximately 1 millimeter. Shape. — Round. Color. — Anthers are colored with a yellow color (RHS Yellow 12 A).

*Pollen production*.—Pollen is abundant and has a yellow color (RHS Yellow 11 A) which may evolve with maturity. The present variety is considered auto-fertile (self-pollinating).

*Pistil*.—Number. — Usually 1. Generally. — Average in size. Length. — Approximately 16.0 to 19.0 millimeters including the ovary. Generally equal or higher to stamen in length, when considered without the ovary. Color. — Considered light green (RHS Yellow Green 150 C) at the beginning of blooming period. Position. — The pistil is positioned above the stamens or at the same level.

*Ovary*.—Height. — Approximately 1.5 millimeters. Diameter. — Approximately 1.5 millimeters. Color. — Green (RHS Yellow Green 144 B). Pubescence. — Absent.

*Stamens*.—Size compared to petals. — The size of stamen is smaller than the size of petals. Length. — Approximately 12.0 to 14.0 millimeters, usually equal to or smaller than the pistil length. Color. — White (RHS White 155 D).

*Average number of stamens per flower*.—Approximately 30 to 38 stamens per flower.

*Stigma*.—Diameter. — Approximately 1.0 millimeter. Color. — Green (RHS Yellow Green 151 B or RHS Yellow Green 151 C). Shape. — Round.

Fruit:

*Maturity when described*.—Firm in ripe conditions (shipping ripe).

*Date of first picking*.—Jul. 14, 2020.

*Date of last picking*.—The date of harvest varies slightly with the prevailing climatic conditions. The 'NECTAMILA' variety has a mid-season date of picking, and a grouped maturity. The maturity is grouped within 9 days and the harvest is generally performed in two runs. Last known picking times carry on from July 14$^{th}$ to Jul. 22, 2020, from July 22$^{nd}$ to Jul. 30, 2021, and from July 21$^{st}$ to July 29$^{th}$ in 2022.

*Size*.—Generally. — Uniform and regular in size, size 2A. Considered medium.

*Average cheek diameter*.—Approximately 64.0 to 65.0 millimeters.

*Average axial diameter*.—Approximately 60.0 to 62.0 millimeters.

*Typical weight*.—Approximately 150.0 to 158.0 grams. This characteristic is high dependent upon the prevailing cultural practices, and therefore is not particularly distinctive of the variety.

*Fruit form*.—Generally. — Round, regular and symmetrical. The fruit is generally uniform in symmetry, viewed from the suture's plane.

*Suture*.—

*Fruit suture*.—The suture is usually wide-mouthed and slightly marked when present, extending from the base to the apex and uniform. No apparent callousing or stitching exists along the suture line. Not pointed. Color. — Luminous purple red (RHS Greyed Purple 187 A).

*Ventral surface*.—Form. — Smooth.

*Apex*.—Not prominent. Mucron. — Absent. Closing of the pistil cavity. — Very good. The pistil cavity is not visible.

*Stem cavity*.—Average depth of the stem cavity is considered medium, about 7.0 to 8.0 millimeters. Average width is between 11.0 and 13.0 millimeters, and the stem cavity is flared.

*Fruit skin*.—Thickness. — Considered medium and strong, and the skin adherence to flesh is medium. Texture. — The pubescence of the skin is absent. The fruit skin is smooth and glabrous. Taste. — Semi-sweet. Tendency to crack. — None observed.

*Color*.—Blush color. — This blush color is a luminous purple red (RHS Greyed Purple 187 A or RHS Greyed Purple 187 B). The purple red blush covers approximately 95% of the fruit skin surface on a red (RHS Greyed Red 179 A) to orange red (RHS Orange red N34 A) background on approximately 5% of the fruit skin surface. The percentage of the blush on the fruit skin surface can vary and is generally dependent upon the prevailing conditions under which the fruit was grown. The pattern of over color of skin is a solid flush. Ground color. — The ground color covers approximately 5% of the fruit skin surface, and is considered red (RHS Greyed Red 179 A) or orange red (RHS Orange Red N34 A). Lenticels. — Absent.

*Fruit stem*.—Medium in length, approximately 13.0 to 15.0 millimeters in length. The fruit stem is smooth with no tearing or detachment.

*Diameter*.—Approximately 2.0 millimeters.

*Color*.—Pale green (RHS Yellow Green 145 A).

*Flesh*.—Ripens. — Very homogenously, slowly. The flesh has a long shelf life and a grouped maturity. Texture. — Firm to very firm, dense, crunchy, melting, before and at harvest maturity stage. Fibers. — Not fibrous. Aroma. — Considered present, with no further characterization. Eating quality. — Considered good to very good, which means a taste perception of high sugar content and developed aromas as stated above. The variety is semi-sweet, sugary and aromatic. Flavor. — Considered semi-sweet. The Brix is generally superior to 12, with values between 12.2 and 13.4, and an average value at 12.8, and acidity is very low. Juice. — Juicy at complete maturity. The juice shows a yellow cream color (RHS Yellow 4 D). Brix. — The medium Brix is 12.8 degrees. This characteristic varies slightly with the number of fruits per tree, prevailing cultural practices and the surrounding climatic conditions. Flesh color. — The flesh is considered yellow orange (RHS Yellow Orange 16 A or RHS Yellow Orange 16 B), usually with varying degrees of red pigmentation (RHS Red 46 A or RHS Red 46 B) depending on the maturity stage. Red coloration of flesh next to skin. — Sparse. Fruit flesh anthocyanin coloration central part of fruit flesh and around the stone. — Medium in intensity, and depending on growing conditions, location, and weather conditions.

Stone:

*Type*.—Semi-Clingstone, more or less semi-adherent depending on the fruit maturity.

*Size*.—Considered medium for the variety. The stone size varies significantly depending upon the tree vigor, crop load and prevailing growing conditions.

*Length*.—Approximately 31.0 millimeters.

*Width*.—Approximately 20.0 to 22.0 millimeters.

*Diameter*.—Approximately 16.0 to 18.0 millimeters.

*Form*.—Obovate.

*Base*.—Straight.

*Apex*.—Shape. — The stone apex is pointed. Shape of stem tip. — Ovate.

*Stone cavity*.—Considered medium in size, with obovate form corresponding to the stone's form and dimensions corresponding to the stone dimensions (approximately 31.0 millimeters in length, 20.0 to 22.0 millimeters in width and 16.0 to 18.0 millimeters in diameter).

*Stone surface*.—Surface texture. — The pit is transversely furrowed on its entire surface. Furrows are deeper and more oblate on lateral sides. Ridges. — The surface texture is generally characterized by more prominent ridges along the ventral edges and at the apical tip.

*Ventral edge*.—Width. — Narrow. Approximately 1.0 millimeter at mid-suture.

*Dorsal edge*.—Shape. — Grooved.

*Stone color*.—The color of the dry stone is generally considered brown (RHS Greyed Orange 164 A or RHS Greyed Orange 164 B).

*Tendency to split*.—Splitting is absent.

*Kernel*.—Size. — The kernel is considered medium. Length. — Approximately 15.0 millimeters. Width. — Approximately 10.0 millimeters. Thickness. — Approximately 5.0 millimeters. Form. — Considered elliptical. Pellicle. — The pellicle of the kernel has a short pubescence. Color. — The kernel skin is light brown colored (RHS Greyed Orange 165 B). The almond, which is the seed of the kernel, is white (RHS White 155 D) and has a sweet taste. The kernel and its embryo are mature at the time of fruit maturity.

*Use*.—The subject variety 'NECTAMILA' is considered to be a yellow nectarine tree having a medium season of maturity, and which produces fruits that are considered firm, attractively colored with a luminous purple red. Fruits have semi-sweet taste and are excellent for uncooked consumption, crunchy or melting when at full maturity. Due to their flesh quality, firmness and density, they can also be commercialized as $4^{th}$ range product (packed fruit or fruit in bags for example). And they are also useful for both local and very long-distance shipping.

*Keeping quality*.—Remarkable. Fruits have a slow maturation and a long shelf life both on the tree after growth completion and after harvesting without alteration. After growth completion, fruits are preserved more than one week. After harvest, fruits are well preserved more than 2 weeks at 2.0 degree Celsius.

*Shipping quality*.—Considered very good. The fruit of the new yellow nectarine variety showed minimal bruising of the flesh or skin damage after being subjected to normal harvesting and packing procedures. Its resistance to handling during harvest and packing and its long shelf life without alteration after harvest easily permit 2 weeks-shipping at 2 degrees Celsius.

*Resistance to insects and disease*.—No particular susceptibilities were noted. The present variety is not very sensitive to Monilia or rot. The pistil cavity is completely closed, generally without any cork formation.

Although the new variety of yellow nectarine tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of yellow nectarine tree named NECTAMILA as illustrated and described herein, characterized by fruits with high eating quality, meaning a taste perception of high sugar content and developed aromas, and very long shelf life without alteration before and after harvesting, with a semi-sweet orange yellow flesh at maturity time, with varying degrees of red pigmentation depending on maturity, and an attractive skin with a very high percentage of luminous purple red blush on skin surface, on a red or orange red background.

* * * * *